United States Patent [19]
Gibson et al.

[11] Patent Number: 6,133,229
[45] Date of Patent: *Oct. 17, 2000

[54] STABILIZATION OF PROTEINS IN SOLUTION

[75] Inventors: Timothy David Gibson; Barry L. Pierce, both of Leeds; Jeanette Irene Webster, Lancashire, all of United Kingdom

[73] Assignee: The University of Leeds Innovations, Ltd., Leeds, United Kingdom

[ * ] Notice: This patent issued on a continued prosecution application filed under 37 CFR 1.53(d), and is subject to the twenty year patent term provisions of 35 U.S.C. 154(a)(2).

[21] Appl. No.: 08/624,585
[22] PCT Filed: Oct. 6, 1994
[86] PCT No.: PCT/GB94/02180
   § 371 Date: Jul. 1, 1996
   § 102(e) Date: Jul. 1, 1996
[87] PCT Pub. No.: WO95/10605
   PCT Pub. Date: Apr. 20, 1995

[30] Foreign Application Priority Data

Oct. 8, 1993 [GB] United Kingdom ............... 9320782

[51] Int. Cl.$^7$ ............................... A61K 38/43; C12N 9/96
[52] U.S. Cl. ................................... 514/2; 514/12; 514/21; 435/188; 525/54.1; 530/408; 530/410
[58] Field of Search ................................... 514/2, 12, 21; 435/188; 525/54.1; 530/408, 410

[56] References Cited

U.S. PATENT DOCUMENTS 4,282,316 8/1981 Modrovich ................................. 435/12
4,318,818 3/1982 Letton et al. .
5,116,729 5/1992 Ismail et al. .
5,240,843 8/1993 Gibson et al. ........................... 435/188

FOREIGN PATENT DOCUMENTS 0190041  8/1986  European Pat. Off. .
2064543  6/1981  United Kingdom .
9005182  5/1990  WIPO .
9114773  10/1991 WIPO .
9211844  7/1992  WIPO .
9412623  6/1994  WIPO .

OTHER PUBLICATIONS

Chang et al., J. Parent. Sci. and Tech., vol. 42, No. 2S pp. S3–S26, 1988.

Gibson et al., Anal. Chim. Acta, vol. 279 No. 1 (Jul. 1993) pp. 185–92.

Caplus AN 1980: 583645, Friedman, Biochem. Biophys. Acta (1980) 619(3) 650–9.

*Primary Examiner*—Bennett Celsa
*Attorney, Agent, or Firm*—Beyer Weaver & Thomas, LLP.

[57] ABSTRACT

A protein stabilizer additive comprises two or more of a tris compound of the formula (1): $(HOCH_2)_3-C-R$, wherein R is: $C_1-C_4$ alkyl, substituted $C_1-C_4$ alkyl, $NH_2$; $NR^1R^2$ wherein $R^1$ and $R^2$ may be independently: H, $C_1-C_4$ alkyl sulphonate, $C_1-C_4$ hydroxyalkyl sulphonate; $C_1-C_4$ alkyl $NHC(CH_2OH)_3$, $C_1-C_4$ alkyl, $C_1-C_4$ hydroxyalkyl; $C_1-C_4$ alkyl carboxylate; a polyelectrolyte; a buffer; and one or more additional components for example divalent metal salts.

9 Claims, No Drawings

STABILIZATION OF PROTEINS IN SOLUTION

This application is a 371 of PCT/GB94/02180 filed Oct. 6, 1994.

BACKGROUND OF THE INVENTION

This invention relates to stabilization of proteins in solution, particularly but not exclusively to stabilisation of enzymes. Alternative proteins include antibodies, antigens, serum compliment, vaccine components and bioactive peptides.

Use of enzymes in analytical applications has become well known because enzymes afford a number of significant advantages over conventional analytical chemistry. Enzymes confer specificity, sensitivity and operate under mild analytical conditions. A major disadvantage of enzyme based assays is that the enzyme component is often unstable. This may lead to degeneration of the reagent during storage and spurious results. Various methods have been used to increase the stability of enzymes including immobilisation, chemical modification by cross-linking, polymer grafting or substitution reactions, physical entrapment or encapsulation in polymer matrices or membranes and the addition of chemicals or solvents to the enzyme preparation. Enzyme preparations for use in analytical methods are often supplied in a dry stabilized form using a combination of chemical additives to promote stability. WO90/05182 and WO91/14773 disclose stabilization of enzymes on drying by mixing aqueous solutions of the enzyme with soluble polyelectrolytes and cyclic polyols before removal of water from the solution. Such compositions have not been found to afford significant stabilization prior to dehydration.

According to a first aspect of the present invention a protein stabilizer additive comprises two or more of:

SUMMARY OF THE INVENTION a. a tris(hydroxymethyl)methyl compound of formula 1;

$$(HOCH_2)_3C-R \tag{1}$$

wherein R is: $C_1-C_4$ alkyl, substituted $C_1-C_4$ alkyl, $NH_2$; $NR^1R^2$ wherein $R^1$ and $R^2$ may be independently: H, $C_1-C_4$ alkyl sulfonate, $C_1-C_4$ hydroxyalkyl sulfonate; $C_1-C_4$ alkyl-NHC(CH$_2$OH)$_3$, $C_1-C_4$ alkyl, $C_1-C_4$ hydroxyalkyl; $C_1-C_4$ alkyl carboxylate;

b. a polyelectrolyte;
c. a buffer; and
d. one or more additional components.

DESCRIPTION OF THE PREFERRED EMBODIMENTS

Component (a) may be referred to as a "tris" compound. Examples of "tris" compounds include: 1,1',1"-tris(hydroxymethyl)ethane; 1,1',1"-tris(hydroxymethyl)propane; tris(hydroxymethyl)aminomethane or salts thereof for example chloride, maleate, phosphate, succinate salts; 1,3-bis[tris(hydroxymethyl)methylamino]propane; bis(2-hydroxyethyl)amino-tris(hydroxymethyl)methane; N-[tris(hydroxymethyl)methyl]-2-aminoethane sulphonate; N-[tris(hydroxymethyl)methyl]-3-aminopropane sulphonate; N-[tris(hydroxymethyl)methyl]-3-amino-2-hydroxypropane sulphonate; N-[tris(hydroxymethyl)methyl]-glycine.

The polyelectrolyte may be a cationic or anionic polyelectrolyte. Amphoteric polyelectrolytes may also be employed. The cationic polyelectrolyte is preferably a polymer with cationic groups distributed along the molecular chain. The cationic groups, which are preferably quaternary ammonium derived functions, may be disposed in side groups pendant from the chain or may be incorporated in it. Examples of cationic polyelectrolytes include: Copolymers of vinyl pyrollidone and quaternary methyl methacrylate e.g., GAFQUAT® series (755N, 734, HS-100) obtained from ISP; substituted polyacrylamides; polyethyleneimine, polypropyleneimine and substituted derivatives; polyamine homopolymers (GOLCHEM® CL118); polyamine co-polymers (e.g., condensates of epichlorohydrin and mono or dimethylamine); polydiallyl dimethyl ammonium chloride (polyDADMAC); substituted dextrans; modified guar gum (substituted with hydroxypropytrimonium chloride); substituted proteins (e.g., quaternary groups substituted on soya protein and hydrolysed collagen); polyamino acids (e.g., polylysine); low molecular weight polyamino compounds (e.g., spermine and spermidine). Natural or artificial polymers may be employed. Cationic polyelectrolytes with MW 150 to 5,000,000, preferably 5000 to 500,000, more preferably 5000 to 100,000 may be employed. An amount of 0.01 to 10% is preferred, more preferably 0.1 to 2% w/v, especially 0.05 to 5%.

The anionic polyelectrolyte is preferably a polymer with anionic groups distributed along the molecular chain. The anionic groups, which may include carboxylate, sulfonate, sulphate or other negatively charged ionisable groupings, may be disposed upon groups pendant from the chain or bonded directly to the polymer backbone. Natural or artificial polymers may be employed.

Examples of anionic polyelectrolytes include: Gantrez (S-series, AN-series); alginic acid and salts; carboxymethyl celluloses and salts; substituted polyacrylamides (eg substituted with carboxylic acid groups); polyacrylic acids and salts; polystyrene sulfonic acids and salts; dextran sulphates; substituted saccharides e.g., sucrose octosulfate; heparin. Anionic polyelectrolytes with MW of 150 to 5,000,000 may be used, preferably 5000 to 500,000, more preferably 5000 to 100,000. An amount of 0.01% to 10% is preferred especially 0.05 to 5% more especially 0.1 to 2% w/v.

The said further component may be selected from the group comprising divalent metal ions, chelators for example EDTA, EGTA or citrate (not with peroxidases) or polyols. Preferred divalent metals include calcium and magnesium salts. Cobalt, zinc or manganese salts may also be employed.

The polyols which may be employed are preferably low molecular weight polyols although polymeric derivatives may be employed. Preferred polyols lower the dielectric of the solution. Such polyols include ethylene glycol, glycerol, erythritol and mannitol. Cyclic polyols which may be employed incorporate one or more alicyclic rings and may have at least one side chain. Preferred cyclic polyols include disaccharides and sugar alcohols, for example lactitol, sorbitol and inositol. Compounds having 2 to 10 hydroxyl groups are preferred. The amount of the polyol may be in the preferred range 1 to 5% more preferably 1 to 20% most preferably 2 to 10% w/v.

Compositions of the present invention stabilize enzymes or other proteins without covalent or otherwise irreversible binding to the latter. The enzymes may be recovered intact from the solution by simple physical means, for example by adjustment of pH to a suitable value followed by salt or solvent precipitation, conveniently with ammonium sulphate.

Compositions of the present invention preferably consist essentially of one or more enzymes or other proteins together with buffers and stabilizers as described in the specification. Naturally occurring complex mixtures such as plasma, serum or other physiological fluids, which may include polyelectrolytes, hydroxy compounds and salts are excluded from the present invention. However immobilised, cross-linked, entrapped or covalently linked proteins are included within the present invention.

Compositions of the present invention are considered to stabilize a protein if the activity of the protein is not significantly diminished after a period of incubation at elevated temperatures in comparison to the protein in the absence of the stabilizers. For example horseradish peroxidase incubated at 60° C. for 120 minutes shows no activity loss with stabilizers of this invention compared to 50% activity loss at 18 minutes under the same conditions.

According to a second aspect of the present invention a method of stabilizing a protein includes the step of contacting the protein with an aqueous solution of an additive as described above.

According to a third aspect of the present invention there is provided use of an additive in accordance with the first aspect of this invention for stabilizing an aqueous protein solution.

The present invention finds particular application in the preparation of analytical assay apparatus. A preferred aspect of the present invention provides an analytical assay formulation incorporating a stabilizer additive as defined above.

The invention is further described by means of example but not in any limitative sense.

The stability of protein solutions in the presence of stabilisers at elevated temperatures was investigated. Buffer solutions containing stabilizers were incubated to the required temperature in a Techne dry heating block. After several minutes incubation the temperature of the buffered mixture was measured using a thermistor. When the temperature was constant at the required level, protein solution was added and the tube was quickly inverted to mix thoroughly and returned to the dry block. Samples were taken at fixed time points thereafter and assayed for activity by standard procedures. All of the results were expressed as the amount of protein activity relative to the zero time activity. Zero time samples were obtained by incubation of the system at 25° C., duplicate samples being taken and assayed for protein activity The present invention is demonstrated by reference to the data in Tables 1 to 20 which show relative specific activities of various proteins as a function of time. Solutions of the proteins without stabilizers underwent rapid denaturation as shown by loss of activity whereas with a polyelectrolyte present greater activity was retained for longer periods. Inclusion of one or more "tris" compounds gave a further increase in stability with the protein activity being retained. Tables 1 and 2 show the effects of a polyelectrolyte (Gafquat 755N), tris compounds and EDTA (as a metal chelator) on the solution stability of alcohol oxidase at 60° C.

TABLE 1

Effect of Stabilizers on Alcohol Oxidase Activity in Solution

| Time (Min) | Control | Polyelectrolyte Alone | +Tris 89 mM | +Tris ethane 89 mM | +Tris propane 89 mM |
|---|---|---|---|---|---|
| 0 | 100.00 | 100.0 | 100.0 | 100.0 | 100.0 |
| 5 | 54.2 | 113.0 | 116.0 | 138.0 | 138.0 |
| 10 | 2.1 | 100.0 | 111.0 | 107.0 | 138.0 |
| 15 | 0 | 80.2 | 92.1 | 95.0 | 123.0 |
| 20 | 0 | 64.5 | 81.6 | 74.9 | 104.0 |
| 25 | 0 | 58.0 | 78.9 | 76.4 | 115.0 |
| 30 | 0 | 38.9 | 26.3 | 59.1 | 96.2 |

The buffer used in this example was 200 mM phosphate pH 8.0.

TABLE 2

Effect of Tris and EDTA with Alcohol Oxidase

| Time (Min) | Control | Polyelectrolyte Alone | +Tris 89 mM and EDTA 1.99 mM | +Tris no EDTA |
|---|---|---|---|---|
| 0 | 100.0 | 100.0 | 100.0 | 100.0 |
| 5 | 61.0 | 113.0 | 162.0 | 116.0 |
| 10 | 15.3 | 100.0 | 168.0 | 111.0 |
| 15 | 10.2 | 80.2 | 154.0 | 92.1 |
| 20 | 6.8 | 64.5 | 134.0 | 81.6 |
| 25 | 6.8 | 58.0 | 140.0 | 78.9 |
| 30 | 5.1 | 38.9 | 123.0 | 26.3 |

The enzyme was alcohol oxidase from Hansenula polymorpha (50 units ml$^{-1}$). The tris solution was buffered to pH 8.0 with phosphoric acid.

The polyelectrolyte was GAFQUAT® 755N (1% w/v).

The enzyme solution was thermally stressed at 60° C. for 30 minutes with the recorded values being the percentage of remaining enzyme activity at 5 minute intervals during the incubation.

TABLE 3

Horseradish Peroxidase in 20 mM Tris pH 8.0

| Time (Min) | No Stabilizers | Gafquat 755 N 0.5% w/v | Ethylene Glycol 10% v/v | Gafquat 755 N 0.5 w/v + Ethylene Glycol 10% v/v |
|---|---|---|---|---|
| 0 | 100 | 100 | 100 | 100 |
| 5 | 77.6 | 88.1 | 72.6 | 90.8 |
| 10 | 69.1 | 76.2 | 63.4 | 78.1 |
| 15 | 57.8 | 63.5 | 57.1 | 70.75 |
| 20 | 48.1 | 59.3 | 52.5 | 63.4 |
| 25 | 46.0 | 53.6 | 48.5 | 59.25 |
| 30 | 39.3 | 48.9 | 43.8 | 55.1 |
| 40 | | 46.5 | 41 | 50.7 |

Table 3 shows stabilization of horseradish peroxidase in 20 mM tris at pH 8.0, at a temperature of 60° C. The combination of the cationic polymer gafquat 755N and ethylene glycol produced better stabilization than either components alone.

TABLE 4

Horseradish Peroxidase in 20 mM Tris Buffer pH 8.0

% Remaining Enzyme Activity

| Time (Min) | No Stabil-izers | Gafquat 755 N 0.5% | $CaCl_2$ 10 mM | Gafquat 755 N 0.5% + Ethylene Glycol 10% v/v + $CaCl_2$ 10 mM |
|---|---|---|---|---|
| 0 | 100 | 100 | 100 | 100 |
| 5 | 77.6 | 88.1 | 81.4 | 99.3 |
| 10 | 69.1 | 76.2 | 85.2 | 96 |
| 20 | 48.1 | 59.3 | 83.4 | 99.3 |
| 30 | 39.3 | 48.9 | 80.8 | 96 |
| 60 | | | 84.2 | 95 |
| 90 | | | 74.8 | 84.5 |
| 120 | | | 80.1 | 87.1 |
| 180 | | | 72.6 | 92.1 |
| 210 | | | 67.2 | 83.4 |
| 240 | | | | 84.9 |

Table 4 shows stabilization of horseradish peroxidase over an extended period at a temperature of 60° C. Calcium chloride alone produced good stabilisation but a combination of cationic polyelectrolyte, ethylene glycol and calcium chloride provided a high level of stabilization for up to 240 minutes.

TABLE 5

Arthromyces Peroxidase

% Remaining Enzyme Activity 20 mM Bis-Tris

| Time (Min) | Phosphate 20 mM No Stabilizers | No Stabil-izers | GAFQUAT ® 755 N 0.5% w/v | $CaCl_2$ 10 mM | GAFQUAT ® 755 N 0.5% w/v + $CaCl_2$ 10 mM |
|---|---|---|---|---|---|
| 0 | 100 | 100 | 100 | 100 | 100 |
| 5 | 68.3 | 97.2 | | | |
| 10 | 63.4 | 92.6 | | | |
| 20 | | 85.53 | 96 | 96.8 | 98.4 |
| 40 | 46.3 | 71.4 | 82 | 84 | 88.6 |
| 60 | | | 72 | 73.2 | 80.9 |
| 150 | | | 36 | 42 | 52 |

Table 5 shows stabilization of arthromyces peroxidase at 4.5 Uml$^{-1}$ in 20 mM bis-tris at pH 7.3 at a temperature of 59° C. Stabilization was obtained with the cationic polyelectrolyte gafquat 755N and also with calcium chloride. However superior stabilization was obtained with a combination of both stabilizers.

TABLE 6

Pig Liver esterase. Gafquat/EDTA

% Remaining Enzyme Activity

| Time (Min) | No Stabil-izers | GAFQUAT ® 0.5% w/v | EDTA 5 mM | GAFQUAT ® 0.5% w/v EDTA 5 mM |
|---|---|---|---|---|
| 0 | 100 | 100 | 100 | 100 |
| 5 | 45.8 | 58.8 | 52.8 | 62.4 |
| 10 | 21.2 | 36 | 40.3 | 41.8 |
| 15 | 13.4 | 24 | 30 | 31.6 |
| 25 | 3.7 | 9.4 | 10 | 8.7 |
| 35 | | 5.6 | | 4.9 |

Table 6 shows stabilization of pig liver esterase with gafquat and EDTA in 20 mM bis-tris pH 7.3 and an incubation temperature of 68.9° C.

TABLE 7

Pig Liver Esterase. Tris (Hydroxymethyl) ethane.

% Remaining Enzyme Activity

| Time (Min) | No Stabil-isers | Tris (OHMe) Et 1% | Tris (OHMe) Et 0.1% |
|---|---|---|---|
| 0 | 100 | 100 | 100 |
| 5 | 45.8 | 60.5 | 65.1 |
| 10 | 21.2 | 26 | 39.6 |
| 15 | 13.4 | 15.2 | 26 |
| 25 | 3.7 | 4.6 | 10.2 |

Table 7 shows stabilisation of pig liver esterase in 20 mM Bis-Tris pH 7.3 with tris (hydroxymethyl) ethane at 68.9° C.

TABLE 8

Stabilisation of Horseradish Peroxidase During Dilution in 20 mM Tris Buffer pH 8.0 at a Temperature of 25° C.

% Relative Specific Activity

| HRP-4 Concen-tration (ug/ml) | No Additive | $CaCl_2$ (10 mM) | DEAE-Dextran MW 500 K (0.5% w/v) | DEAE-Dextran MW 500 K (0.5% w/v) + Ethylene Glycol (10% v/V) + $CaCl_2$ (10 mM) |
|---|---|---|---|---|
| 0.732 | 15 | 80 | 98 | 100 |
| 1.83 | 44 | 90 | 99 | 98 |
| 3.66 | 64 | 95 | 100 | 102 |
| 7.32 | 103 | 97 | 100 | 101 |
| 18.3 | 97 | 105 | 102 | 101 |
| 36.6 | 100 | 98 | 101 | 99 |

Table 8 shows the stabilisation of horseradish peroxidase in 20 mM tris at pH 8.0. DEAE-dextran both alone and in the presence of ethylene glycol and calcium chloride surprisingly afforded stability at extreme dilutions.

TABLE 9

The Stability of Dilute Solutions of Horseradish Peroxidase (3.66 ug/ml) At 37° C.

% Remaining Enzyme Activity

| Time (Min) | No Stabil-isers | DEAE-Dextran MW 500 K (0.5% w/v) | DEAE-Dextran MW 500 K (0.5% w/V) + Ethylene Glycol (10% v/v) + $CaCl_2$ (10 mM) |
|---|---|---|---|
| 0 | 100 | 100 | 100 |
| 5 | 62 | 80 | 98 |
| 10 | 56 | 79 | 101 |
| 15 | 51 | 77 | 102 |
| 20 | 47 | 81 | 98 |
| 30 | 40 | 79 | 103 |
| 40 | 35 | 75 | 101 |
| 50 | 30 | 76 | 103 |
| 60 | 23 | 75 | 101 |
| 90 | | 71 | 100 |
| 120 | | 70 | 96 |
| 150 | | 65 | 106 |
| 180 | | 60 | 103 |

Table 9 shows stability of very dilute solutions of horseradish peroxidase (3.66 µg/ml$^{-1}$) at 37° C. A combination of DEAE-dextran, ethylene glycol and calcium chloride afforded excellent stabilisation for up to 180 minutes.

TABLE 10

Trypsin Autodigestion (Phosphate Buffer)

% Remaining Enzyme Activity

| Time (Min) | No Stabilisers | Gafquat 755 N 0.5% w/v | DEAE-Dextran 0.5% w/v |
|---|---|---|---|
| 0 | 100 | 100 | 100 |
| 5 | 55.6 | 82.8 | 66.7 |
| 10 | 40.2 | 61.8 | 57.2 |
| 15 | 35.5 | 50.6 | 45.7 |
| 20 | 26.4 | 48.3 | 42.3 |
| 35 | | | |

Tables 10 and 11 show that the presence of polyelectrolyte retards autodegradation of trypsin, this effect was enhanced in the presence of tris stabiliser.

TABLE 11

Trypsin Autodigestion (Tris Buffer)

% Remaining Enzyme Activity

| Time (Min) | No Stabilisers | GAFQUAT ® 755 N 0.5% w/v | DEAE-Dextran 0.5% w/v |
|---|---|---|---|
| 0 | 100 | 100 | 100 |
| 5 | 72.3 | 95 | 90.8 |
| 10 | 54.8 | 82.8 | 73.6 |
| 15 | 50.5 | 69 | 60.9 |
| 20 | 25.4 | 57.1 | 54.3 |
| 35 | 17.7 | 40 | 39.6 |

TABLE 12

Alkaline Phosphatase (Bovine)

% Remaining Enzyme Activity

| Time (Min) | No Stabilisers | $MgCl_2$ 10 mM Ethylene Glycol (10% v/v, 0.5% w/v) BSA and DEAE-Dextran (0.5 w/v) |
|---|---|---|
| 0 | 100 | 100 |
| 5 | 61.4 | 88.5 |
| 10 | 45.7 | 72.5 |
| 15 | 42.1 | 66.4 |
| 20 | 36.8 | 61.9 |
| 40 | 30.1 | 50 |

Table 12 shows stabilisation of bovine alkaline phosphatase in 50 mM tris buffer at pH 8.0 and 61° C. Stabilisers comprising magnesium chloride, ethylene glycol, Bovine Serum Albumin and DEAE-dextran provided enhanced stabilisation.

TABLE 13

The Effect of Combinations of Stabilisers on the Stability of Horseradish Peroxidase(Biozyme) Solutions (20 mM Tris/HCl Buffer pH 8.0) at 69° C.

% Remaining Enzyme Activity

| Time (Min) | No Stabiliser | DEAE-Dextran MW 500K (0.5% w/v) | Ethylene Glycol (10% v/v) | $CaCl_2$ (10 mM) | Ethylene Glycol (10% v/v) + $CaCl_2$ (10 mM) | DEAE-Dextran MW 500K (0.5 w/v) + $CaCl_2$ (10 mM) | DEAE-Dextran MW 500K (0.5% w/v) + Ethylene Glycol (10% v/v) + $CaCl_2$ (10 mM) |
|---|---|---|---|---|---|---|---|
| 0 | 100 | 100 | 100 | 100 | 100 | 100 | 100 |
| 5 | 78 | 88 | 94 | | | | |
| 10 | 69 | 75 | 76 | | | | |
| 15 | 58 | 67 | 64 | | | | |
| 20 | 48 | 61 | 61 | 98 | 103 | 99 | 101 |
| 25 | 45 | 55 | 57 | | | | |
| 30 | 39 | 50 | 53 | | | | |
| 40 | | | | 78 | 101 | 99 | 103 |
| 60 | | | | 97 | 101 | 100 | 101 |
| 80 | | | | 92 | 100 | 97 | 102 |
| 120 | | | | 85 | 96 | 94 | 103 |
| 180 | | | | 79 | 90 | 85 | 97 |
| 240 | | | | | | 80 | 92 |

Table 13 shows the effect of combinations of stabilisers on the stability of horseradish peroxidase in 20 mM tris/HCl buffer at pH 8.0 and 69° C. This example shows the use of substituted dextrans as polyelectrolytes, a good stabilisation chloride in combination.

TABLE 14

The Stability of HRP-4 (Biozyme) Solutions (20 mM Tris/HCI Buffer pH 8.0) at 50° C.

% Remaining Enzyme Activity

| Time (Days) | No Stabiliser | DEAE-Dextran MW 500 K (0.5% w/v) + Ethylene Glycol (10% v/v) + CaCl$_2$ (10 mM) |
|---|---|---|
| 0 | 100 | |
| 0.0347 | 90.3 | |
| 0.056 | 95.1 | |
| 0.0764 | 90.3 | |
| 0.0972 | 82 | |
| 0.118 | 69.4 | |
| 0.139 | 65.4 | |
| 0.167 | 63.8 | |
| 0.26 | 46.3 | |
| 0.27 | 49.3 | |
| 0.29 | 38.4 | 101 |
| 1 | | |
| 2 | | 99 |
| 6 | | 106 |
| 8 | | 102.8 |

Table 14 shows stabilisation of horseradish peroxidase solutions in 20 mM tris/HCl buffer at pH 8 and 50° C. Degradation without stabiliser is rapid but good stabilisation was obtained at periods up to 8 days using a combination of DEAE-dextran, ethylene glycol and calcium chloride.

TABLE 15

The Effect of Temperature on the Stability of HRP-4 (Biozyme) Solutions (20 mM Tris/HCI Buffer pH 8.0) in the Presence of Ethylene Glycol (10% v/v), DEAE-Dextran MW 500 K (0.5% w/v) and Calcium Chloride (10 mM)

% Remaining Enzyme Activity

| Time (Min) | 85.5° C. | 80.5° C. | 75.5° C. | 70.5° C. |
|---|---|---|---|---|
| 0 | 100 | 100 | 100 | 100 |
| 3 | 71 | | | |
| 5 | | 80 | 91 | |
| 6 | 56 | | | |
| 9 | 39 | | | |
| 10 | | 64 | 85 | 102 |
| 12 | 30 | | | |
| 15 | 28 | 53 | 82 | |
| 18 | 25 | | | |
| 20 | | 47 | 77 | 100 |
| 21 | 22 | | | |
| 25 | | 40 | | |
| 30 | | 33 | 73 | 103 |
| 40 | | 30 | 68 | |
| 50 | | 25 | 63 | 100 |
| 60 | | | 58 | |
| 70 | | | | 99 |
| 110 | | | | 100 |
| 130 | | | | 93 |
| 150 | | | | 93 |
| 170 | | | | 88 |

Table 15 shows the effect of temperature on the stability of horeradish peroxidase solutions (20 mM tris/HCl buffer pH 8.0) in the presence of ethylene glycol, DEAE-dextran (MW 500K) and calcium chloride.

TABLE 16

Long Term Stability of HRP-4 Solutions

% Remaining Enzyme Activity

| Time (Days) | No Stabiliser; 37° C. | Stabilisation Buffer; 37° C. | No Stabiliser; Room Temperature | Stabilisation Buffer; Room Temperature |
|---|---|---|---|---|
| 0 | 100 | 100 | 100 | 100 |
| 6 | 90 | 101 | 96 | 99 |
| 15 | 85 | 98 | 93 | 100 |
| 21 | 76 | 99 | 86 | 101 |
| 33 | 32 | 99 | 82 | 101 |

Table 16 illustrates long term stabilisation of horseradish peroxidase solutions at different temperatures. The stabilisation buffer was the same as for example 15.

TABLE 17

The Stabilisation of HRP Activity of Antibody/HRP Conjugate (Sigma) Solutions (20 mM Tris/HCI Buffer pH 8.0) at 50° C.

% Remaining Enzyme Activity

| Time (Hours) | No Stabiliser | DEAE-Dextran MW 500K (0.5% w/v) + CaCl$_2$ (10 mM) | DEAE-Dextran MW 500K (0.5% w/v) + CaCl$_2$ (10 mM) + Ethylene Glycol (10% v/v) |
|---|---|---|---|
| 0 | 100 | 100 | 100 |
| 0.5 | 86 | 99.4 | 100.6 |
| 20.8 | 35.9 | 80.1 | 100 |
| 48 | | | 99 |
| 72 | | | 97.6 |

Table 17 illustrates stabilisation of horseradish peroxidase activity of antibody-horseradish peroxidase conjugate solutions using the following stabiliser: CaCl$_2$ 10 mM, ethylene glycol 10% v/v, DEAE-dextran 0.5% w/v, Buffer Tris/HCl 20 mM pH 8.0

The stabilisation of the HRP label of the IgG-HRP conjugate (SIGMA® A 6029) with the combination described resulted in loss of activity over 3 days incubation of 50°C.

TABLE 18

Galactose Oxidase: Stability at 66.5° C. in 20 mM Tris phosphate pH 7.84

% Remaining Enzyme Activity

| Time | No Stabiliser | Gantrez S-97 0.5% w/v |
|---|---|---|
| 0 | 100 | 100 |
| 5 | 87.9 | 96.1 |
| 10 | 69.5 | 82.1 |
| 15 | 58.6 | 75.6 |
| 20 | 53.2 | 68 |

TABLE 19

Galactose Oxidase: Stability at 66.4° C. in 20 mM Tris phosphate pH 7.84

| | % Remaining Enzyme Activity | |
|---|---|---|
| Time | No Stabilisers | Sodium Alginate 0.2% w/v |
| 0 | 100 | 100 |
| 5 | 87.9 | 114.5 |
| 10 | 69.5 | 102.8 |
| 15 | 58.6 | 99.8 |
| 20 | 53.2 | 79.5 |

TABLE 20

Alcohol Oxidase in 20 mM Bis-Tris pH 6.0

| | % Remaining Enzyme Activity | |
|---|---|---|
| Time | No Stabilisers | Carboxymethyl Cellulose 0.125% |
| 0 | 100 | 100 |
| 5 | 15 | 37.1 |
| 10 | 10.7 | 27.9 |
| 20 | 8.9 | 21.8 |
| 30 | 7 | 19 |

What is claimed is:

1. A method of stabilizing an aqueous enzyme comprising the step of contacting the enzyme selected from the group consisting of peroxidase enzymes, alkaline phosphatase enzymes and antibody conjugates thereof with an aqueous solution of a protein stabilizer additive comprising:

a. a tris(hydroxymethyl)methyl compound of formula 1;

(HOCH$_2$)$_3$C—R        (1)

wherein R is: NH$_2$; NR$^1$R$^2$ wherein R$^1$ and R$^2$ may be independently: H, C$_1$–C$_4$ alkyl, C$_1$–C$_4$ hydroxyalkyl, C$_1$–C$_4$ alkyl sulfonate, C$_1$–C$_4$ hydroxyalkyl sulphonate; C$_1$–C$_4$ alkyl NHC(CH$_2$OH)$_3$; C$_1$–C$_4$ alkyl carboxylate;

b. a cationic polyelectrolyte selected from the group consisting of copolymers of vinyl pyrollidone and quaternary methyl methacrylate and DEAE dextran;

c. a polyol selected from the group consisting of glycerol, ethylene glycol, sorbitol and lactitol; and d. one or more salts selected from the group consisting of salt of calcium, magnesium and cobalt.

2. A method as claimed in claim 1 wherein the tris (hydroxymethyl)) methyl compound is selected from the group consisting of: tris(hydroxymethyl)aminomethane and salts thereof selected from the group consisting of chloride, maleate, phosphate, succinate salts; 1,3-bis{tris(hydroxymethyl)methylamino}propane; bis(2-hydroxyethyl)amino-tris(hydroxymethyl)methane; N-{tris(hydroxymethyl)methyl}-2-aminoethane sulfonate; N-{tris(hydroxymethyl)methyl}-3-aminopropane sulfonate; N-{tris(hydroxymethyl)methyl}-3-amino-2-hydroxypropane sulfonate; and N-{tris(hydroxymethyl)methyl}-glycine.

3. A method as claimed in claim 1 wherein the cationic polyelectrolyte has a molecular weight of 150 to 5,000,000 Daltons.

4. A method as claimed in claim 1 wherein the cationic polyelectrolyte is present in an amount of 0.01 to 10% w/v.

5. A method as claimed in claim 1 wherein the polyol is present in an amount of 0.1 to 25% w/v.

6. A method as claimed in claim 1 wherein said peroxidase enzyme is selected from the group consisting of horseradish peroxidase and arthromyces peroxidase.

7. A method as claimed in claim 2, wherein the tris (hydroxymethyl) compound is selected from the group consisting of tris(hydroxymethyl)aminomethane and salts thereof selected from the group consisting of chloride, maleates, phosphate, succinate salts; 1,3-bis{tris(hydroxymethyl)methylamino}propane; and bis(2-hydroxyethyl)aminotris(hydroxymethyl)) methane.

8. A method as claimed in claim 1, wherein said enzyme is horseradish peroxidase, said tris is 20 mM tris/HCL buffer pH 8.0, said polyol is ethylene glycol, said cationic polyelectrolyte is DEAE-dextran (MW 500K), and said salt is calcium chloride.

9. A method as claimed in claim 8, wherein at least 99% of the enzyme's activity is retained after 33 days at 37° C.

* * * * *